(12) United States Patent
Feller (10) Patent No.: US 6,510,734 B1
(45) Date of Patent: *Jan. 28, 2003

(54) METHOD OF ASSESSING THE EFFECTS OF YARN DEFECTS ON TEXTILE FABRICS

(75) Inventor: Peter Feller, Benglen (CH)

(73) Assignee: Zellweger Luwa AG, Uster (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,764

(22) PCT Filed: Jun. 2, 1997

(86) PCT No.: PCT/CH97/00222
§ 371 (c)(1),
(2), (4) Date: Dec. 3, 1998

(87) PCT Pub. No.: WO97/47959
PCT Pub. Date: Dec. 18, 1997

(30) Foreign Application Priority Data

Jun. 12, 1996 (CH) ............................................. 1472/96

(51) Int. Cl.$^7$ ............................. G01L 5/04; G01N 21/86
(52) U.S. Cl. ..................... 73/160; 73/159; 356/238.2; 356/430; 250/559.05
(58) Field of Search ................ 73/159, 160; 356/238.2, 356/430; 250/559.05

(56) References Cited

U.S. PATENT DOCUMENTS

| 4,984,181 | A | | 1/1991 | Kliman et al. ............... 364/518 |
|---|---|---|---|---|
| 5,146,550 | A | * | 9/1992 | Furter et al. ................. 345/440 |
| 5,319,578 | A | | 6/1994 | Lawson et al. .............. 364/563 |
| 5,570,188 | A | * | 10/1996 | Nevel et al. ................. 356/385 |
| 5,671,061 | A | | 9/1997 | Hoeller ........................ 356/429 |
| 6,130,746 | A | * | 10/2000 | Nevel et al. .............. 356/238.2 |

FOREIGN PATENT DOCUMENTS

| DE | 27 44 241 | 4/1979 |
|---|---|---|
| DE | 41 31 664 | 3/1993 |
| DE | 43 41 685 | 6/1995 |
| JP | 60-167968 | 8/1985 |
| JP | 08-043318 | 2/1996 |

* cited by examiner

Primary Examiner—Hezron Williams
Assistant Examiner—Michael Cygan
(74) Attorney, Agent, or Firm—Burns, Doane, Swecker & Mathis, L.L.P.

(57) ABSTRACT

The invention relates to a method for assessing the effect of yarn defects on textile fabrics, which are to be produced from a given yarn, by simulating an image of the fabric. So that assessment of simulated textile fabrics may be carried out with greater reliability and more easily, a first image (51) of the fabric is generated by simulation based on parameters or measured signals of the given yarn. A second image (52) of the fabric is generated by simulation based on parameters of a reference yarn and finally the first image is compared with the second image.

8 Claims, 7 Drawing Sheets

PRIOR ART

METHOD OF ASSESSING THE EFFECTS OF YARN DEFECTS ON TEXTILE FABRICS

The invention relates to a method of assessing the effect of yarn defects on textile fabrics, by simulating an image of the fabric based on a predetermined yarn.

Such a method is known from EP-A-578975 and related U.S. Pat. No. 5,671,061 in which in a first step a yarn is examined by a measuring element with respect to parameters which are connected with the volume and/or the surface of the yarn. In a second step the parameters are converted into grey or color values and these values are associated with pixels. Finally the pixels are reproduced on a display screen and/or a printer. An image is thereby generated which represents a simulation of a woven or knitted fabric produced from the examined yarn.

A disadvantage of the known method consists in the fact that this simulation does not correspond precisely to the image of an actual woven or knitted fabric, since simplifying assumptions are made for the purpose of simulation, which assumptions have the above effect. Such an assumption comprises representing in the simulation yarn portions lying parallel with each other and weighting or even completely ignoring cross-weaving between warp and weft yarns. Thus, the assessment of a simulated woven or knitted fabric is made more difficult. Correct assessment therefore requires a certain amount of practice.

The object which the invention is intended to achieve comprises removing the above-mentioned disadvantages and providing a method with which assessment of simulated textiles fabrics may be effected with greater certainty.

The object is achieved in that an image of a woven or knitted fabric, which has arisen through known simulation, wherein parameters of a real, measured yarn are taken into consideration, is compared with the image of a woven or knitted reference fabric for which the parameters used are those of a reference yarn standardized according to quality or graded according to statistical data. The reference yarn is characterized by parameters which correspond, for example, to average values such as may be inferred from published statistics. The parameters of the reference yarn may thus be obtained by measuring a real reference yarn or by calculation from given statistical values.

In other words, an image of a woven reference fabric is produced which is more like the image of the fabric woven from given yarn and with which the image of the known simulated woven fabric may be compared. The image of the woven reference fabric may be achieved by mapping a so called yarn diagram, which is compiled with a reference yarn. Or, the image of the reference yarn may be generated by simulation of a woven fabric from the reference yarn. Simulation of the reference yarn may be effected by calculation of yarn parameters or by measuring the parameters of a real reference yarn. The best result is achieved if two textile fabrics are simulated in the same way, wherein the only difference is in the values for the parameters, wherein one series of values originates from a given yarn and the other values from a reference yarn.

The advantages achieved by the invention are in particular that the woven or knitted reference fabric is represented in precisely the same manner as the simulated woven or knitted fabric on a screen or on paper, such that deviations between the images directly indicate deviations between real knitted and woven fabrics and as a result different values are considered for the selected parameters. For these directly comparable images, the observer, who has to assess these, may also apply his own subjective criteria, which he may use for assessment. He need not fear any distortion of his criteria, as would have to be taken into account when the images are not directly comparable.

The invention is described in more detail below with the aid of an example and with reference to the enclosed Figures, in which.

The method according to the invention comprises on the one hand the known simulation of an image of a textile fabric which is constructed from a given yarn whose parameters are measured and on the other hand the simulation of an image of a textile fabric which is constructed from a reference yarn. The possibility here arises of measuring the parameters of such a reference yarn, which will not be described in any more detail because such a measurement does not differ from the measurement of any other yarn, or to calculate the parameters of a reference yarn. This second possibility will be described below in more detail with reference to the Figures. The necessary method steps will also be explained with the aid of the individual Figures.

Figure 1:
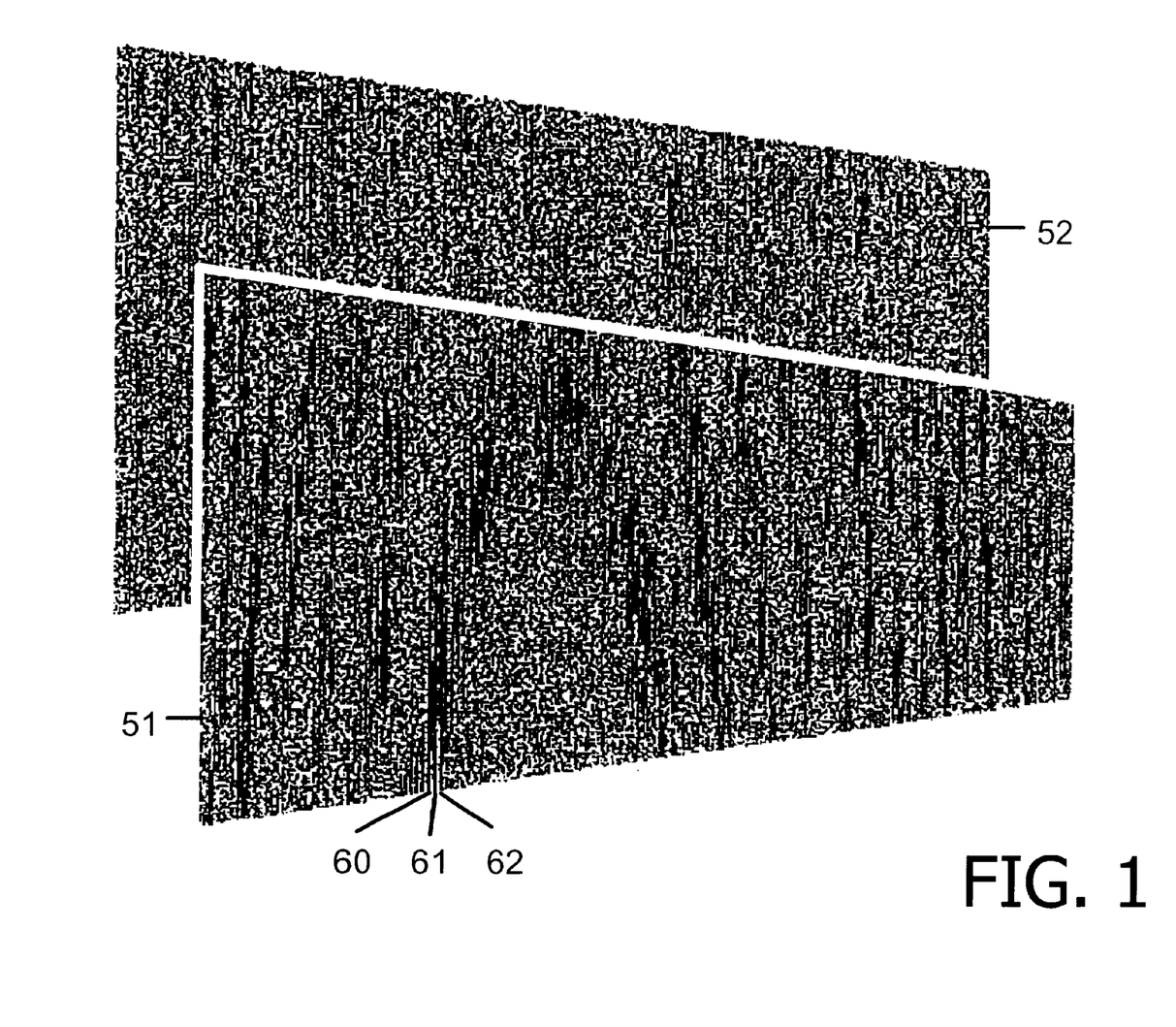
FIG. 1 shows images of a yarn diagram and a simulated yarn diagram.

FIG. 1 shows an image 52 of a fabric which is constructed according to the present invention from a reference yarn by simulation. The reference yarn may be provided by measured parameters or by calculated parameters. This image is intended to act as a reference for images of fabrics which are constructed from other yarns by simulation, wherein the yarns are simulated on the basis of measured values from a real yarn. Such an image 51 is likewise shown for comparison. A comparison of the two images, as may be carried out by the human eye for example, permits recognition of deviations in the images 51, 52 and the further evaluation thereof. For example, in the image 51 a Moire effect may be seen, the possible causes of which are known per se and may be traced back, for example, to periodic defects in the yarn.

Figure 2:
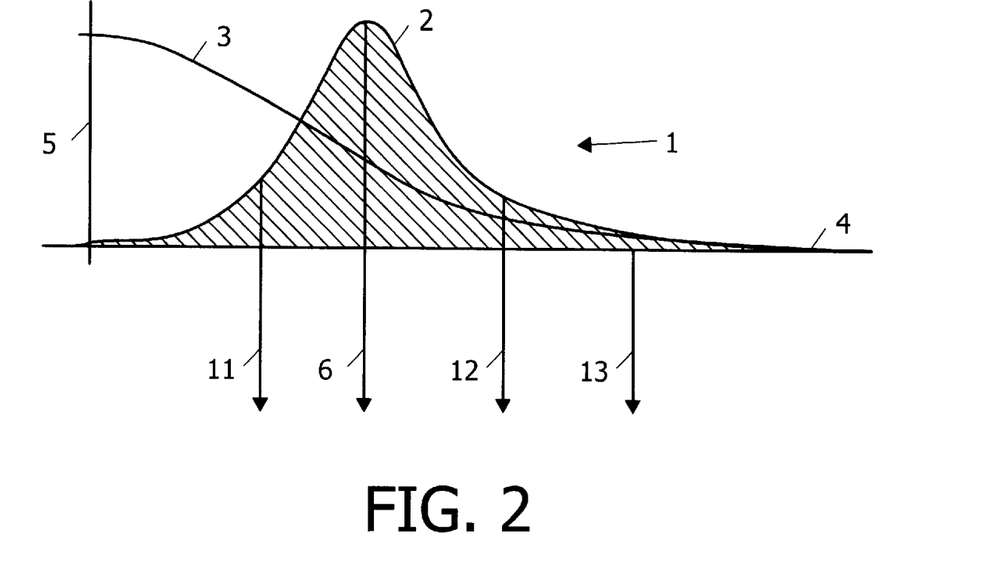
FIG. 2 shows a so called staple diagram.

FIG. 2 shows a so-called staple diagram 1, comprising a curve 2 relating to frequency distribution and a curve 3 acting as a cumulative frequency distribution curve. The staple diagram is the starting point for calculation of the yarn parameters. Curves 2 and 3 are plotted over a horizontal axis 4, along which markings or values for the lengths of textile fibers are entered. Along a vertical axis 5 markings or values are provided for the percentage of fibers of a certain length. It is thus easy to see from curve 2 that the largest percentage of the fibers of a staple from which the values derive exhibit the length corresponding to the value at the point 6. From curve 3 it may be seen that 100% of the fibers are at least infinitely short, but that there are no infinitely long fibers. Such staple diagrams can either be found in expert literature or may be measured from raw materials with commercial apparatuses. Such apparatuses are sold by Zellweger Uster under the name AFIS or AL100. The staple diagram is one of the bases for calculation of the yarn parameters. It provides values which are characteristic of a raw material, here in particular a reference raw material used as a starting point, i.e. it indicates to what extent an ideal distribution of the fibre lengths can be used as a starting point for the reference yarn. Depending on its composition, the yarn which is produced from this raw material then comprises more or less pronounced quasiperiodic irregularities which may be represented in spectrograms.

Figure 3:
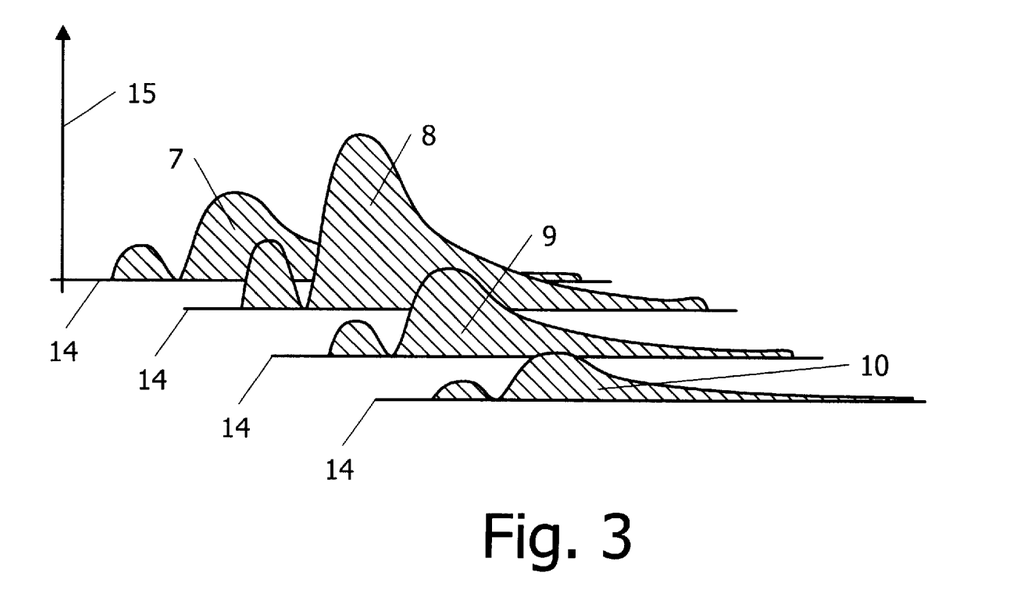
FIG. 3 shows several spectrogram curves for various staple lengths.

FIG. 3 shows horizontally and vertically displaced representations of four spectrogram curves 7, 8, 9, 10 each for a yarn which consists of fibers of constant length, wherein the length of the fibers for these yarns increases from spectrogram curve 7 to spectrogram curve 10. Lengths of fibers for these yarns may, for example, be read off at points 6, 11, 12 and 13 of the axis 4 in FIG. 2. Along the axes 14 there are plotted values for wavelengths and along an axis 15 there are plotted values for amplitudes or power density (as detected by evenness testers). From these spectrogram curves 7 to 10 it is possible to see, for example, that the amplitudes of the irregularities in the yarn with long fibers are relatively small, as (&.b spectrogram curve 10 shows, but are larger for short fibers, as shown in spectrogram curves 8 and 9. The formula $$p(f) = \frac{1}{n}\sin^2\left(\frac{\pi f L}{v}\right) \quad (A)$$

where p is the power density, as measured in a known yarn evenness tester, n is the number of fibers in a yarn cross section, L is the length of the fibers, f is the measuring frequency and vis the measuring speed of the yarn, represents the spectrogram curves as yielded by known yarn evenness testers. In some evenness testers, the power is measured with band-pass filters which have a constant relative and width. For example, 5 band-pass filters are arranged per octave, the band boundaries of which touch. This results in a stepped spectrogram curve instead of the continuous curve shown here.

A spectrogram continuous in form is based on the formula $$a(\log\lambda) = c\frac{\sin\left(\pi\frac{L}{\lambda}\right)}{\sqrt{\lambda/L}} \quad (B)$$

where c is a constant of proportionality.

Finally, since on the one hand for the comparison of the simulated fabric parameters measured with known yarn testers are used, it is advantageous for the simulation of the reference yarn and the reference image on the other hand also to work as far as possible with values as determined in the yarn testers.

Thus, known yarn testers provide representations of spectrograms which give the root of the power instead of the power density or the wavelength in stead of the frequency on a logarithmic scale. This is taken into account in the above illustration of formula (B). From spectrogram curves 7 to 10 for yarns which are constructed from fibers of equal length, a spectrogram curve may be derived for a yarn which consists of fibers of different lengths, as is usual with real yarns.

Figure 4:
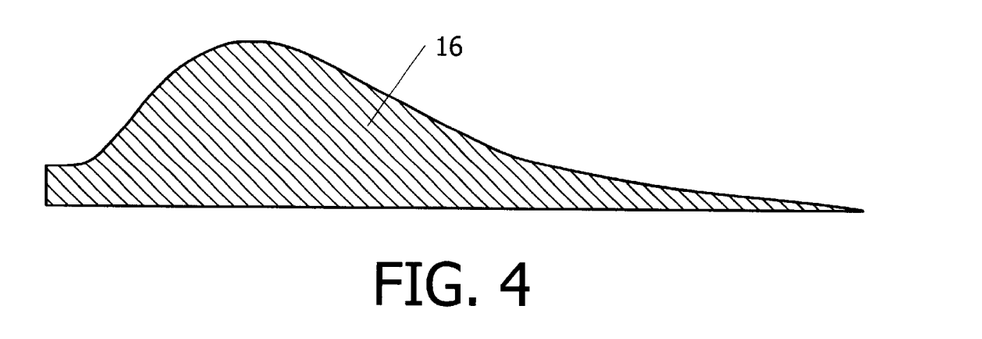
FIG. 4 shows a spectrogram curve for yarn made of randomly distributed fibers of different lengths.

FIG. 4 therefore shows a spectrogram curve 16 which is produced by superposing several spectrogram curves, such as spectrogram curves 7, 8, 9, 10 for example. From the staple diagram (FIG. 1) it is possible to infer frequency values from curves 2 or 3 for fibre length values which are given, for example, at constant spacing along the axis 14. With these values the spectrograms may be weighted for the relevant fibre lengths. The spectrogram curve 16 is calculated according to the following formula (C) for the weighted spectrogram curve:

$$a(\log\lambda) = c\sqrt{\sum_{i=0}^{n} h_i \frac{\sin^2(\pi\lambda/(L_0 k^i))}{\lambda/(L_0 k^i)}} \quad (C)$$

where k is the logarithm of the length ratio of adjacent classes $L_i/L_{i+1}$ and h is the frequency of fibre number as a function of the fibre length, as may be inferred from FIG. 2.

Figure 5:
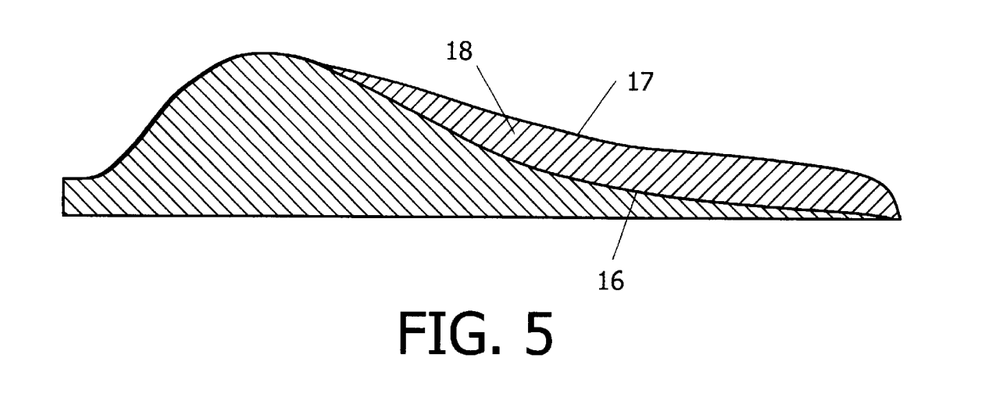
FIG. 5 shows a spectrogram curve taking into consideration process-determined long wavelength variations.

FIG. 5 shows a spectrogram curve 17, which is derived from spectrogram curve 16. In spectrogram curve 17 defects are taken into account which a yarn may exhibit as a consequence of production conditions which are not ideal. Such defects, caused or not rectified by production machines for example, are generally of long wavelength, for which reason the spectrogram curve 17 deviates from spectrogram curve 16 especially in an area 18.

The deviation in the area 18 may be determined by values from known length variation curves CV(L) and mass variation curves CVm, as explained in more detail below.

Figure 6:
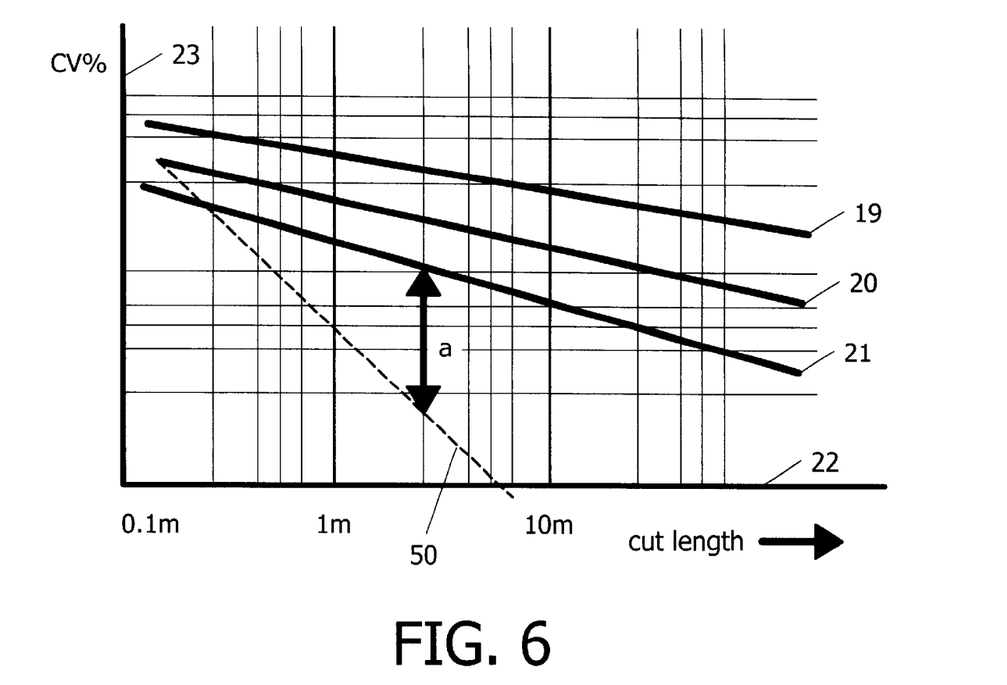
FIGS. 6 and 7 are each representations of variation curves.

FIG. 6 shows three limits 19, 20 and 21 which restrict fields in which may lie length variation curves CV(L) for yarns of different qualities. These are plotted with values for cut yarn lengths over a horizontal axis 22 and with values for percentage deviations from an average value on a vertical axis 23. The limit 19 relates to yarns of the poorest quality and limit 21 to yarns of the best quality. From this it may be seen that in the case of yarns of 15 good quality the deviations from the average value decrease more rapidly as the cut length increases than is the case for yarns of poorer quality. In addition, a length variation curve 50 for an ideal yarn is entered. Since it is known from FIGS. 3 and 4 that long wavelength defects in the yarn are of lower amplitude than short wavelength defects, FIG. 6 indicates that, in the case of poor quality yarns caused by poor production machinery, long wavelength defects are also of amplitudes which cannot be ignored. Therefore, the amplitude values from the spectrogram curve 16 have to be corrected or multiplied by a factor which takes into account the long wavelength defects actually present in the non-ideal yarn. This correction is effected in the descending branch of the spectrogram curve 16, especially for cut lengths over ca. 0.5 m in the area 18. The factor is produced for different cut lengths and results from the distance a between the length variation curve 50 and the selected limit 21, 20, 19. Since the values are plotted logarithmically along both axes 22, 23, this distance a may be converted directly by delogarithmisation into a factor. The spectrogram curve 17 is obtained from spectrogram curve 16 by this correction.

Figure 8:
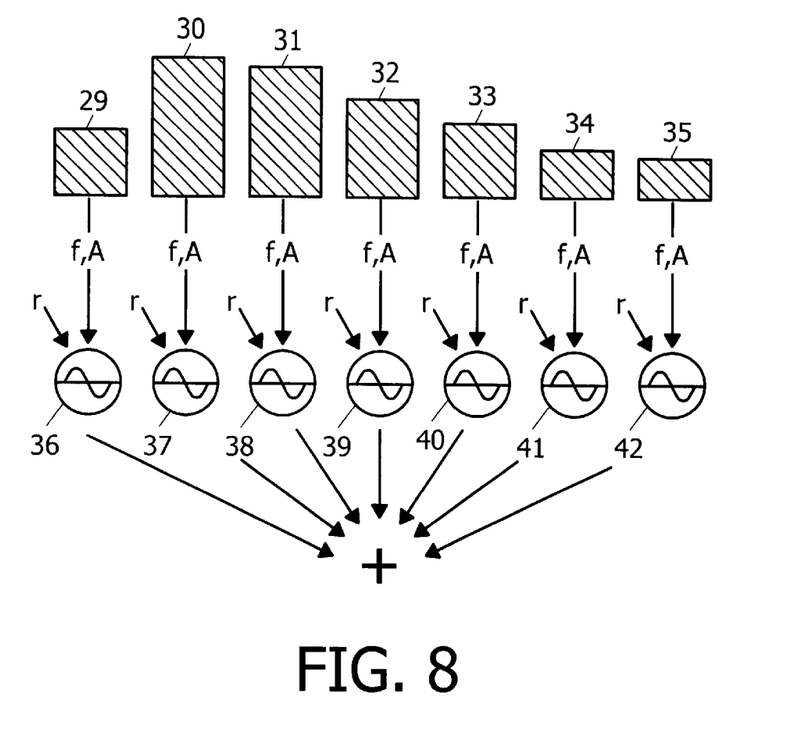
FIG. 8 is a schematic representation of an inverse Fourier transform.
Figure 10:
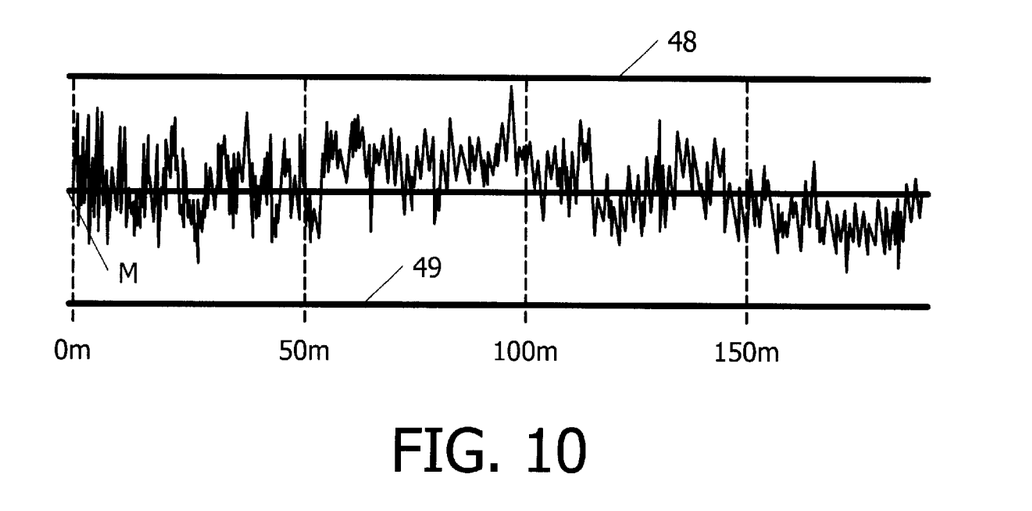
FIG. 10 is a mass-variation curve for a yarn.

From existing spectrogram 17 a yarn signal has then to be produced by calculation, as could also be produced by a yarn tester. This is shown in FIG. 8. To this end, an inverse Fourier transform is used, which, from signals in the spectral region, results in an output signal which represents cross-sectional or mass deviations along the yarn. To this end, the spectrogram curve 17 is divided logarithmically into classes which are here represented by rectangles 29 to 35. on the logarithmic scale these classes exhibit equal lengths amongst themselves. Each class 29 to 35 thus also represents a wavelength range which may also be further subdivided into several channels, thus, for example, into 5 to 10 channels per octave. A sine-wave generator 36 to 42 is allocated to each class 29 to 35, the frequency of which sine-wave generator 36 to 42 is in inverse proportion to the wavelength of the class and the amplitude of which is proportional to the height of the class or to the frequency (corresponding to the height of the rectangle) of the deviations represented by the class. Each generator 36 to 42 thus generates a sinusoidal signal, which signals are combined by superposition, such that a single output signal arises which represents mass deviations from an average value over time, as is shown in FIG. 10 for example. For this output signal a coefficient of variation may be determined in a manner known per se.

Figure 7:
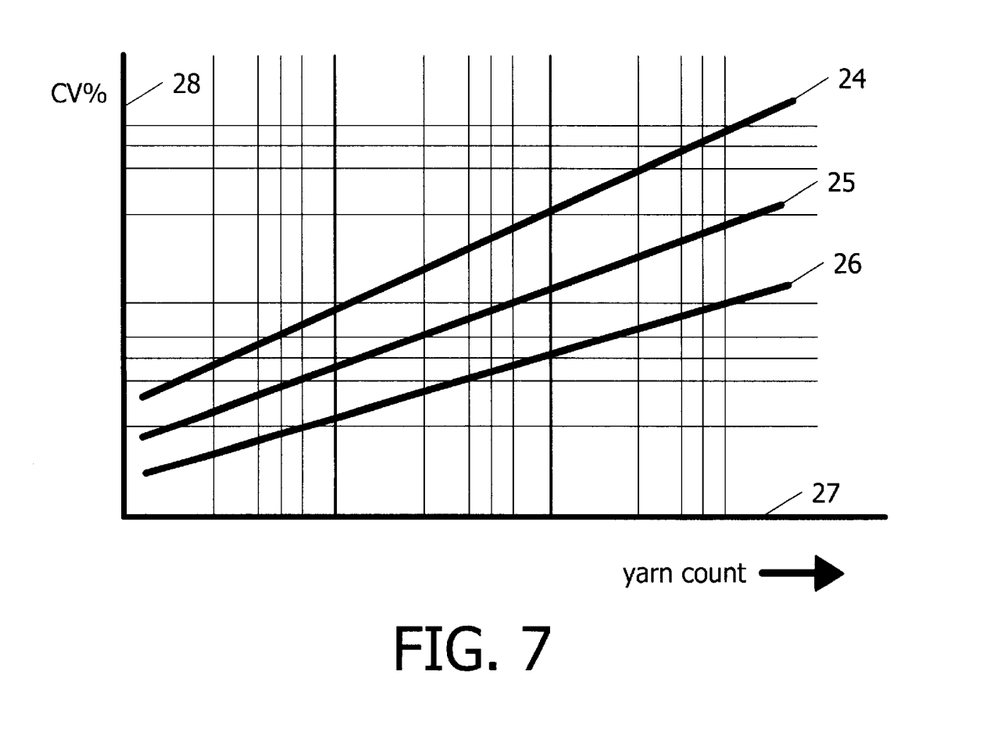

Such coefficients of variation are also recorded for known yarns in FIG. 7. FIG. 7 shows three limits 24, 25 and 26 within which there may lie values for the mass variation of yarns of different qualities. These are plotted with values for the so-called yarn number or fineness (which is in inverse proportion to the thickness) over a horizontal axis 27 and with values for coefficients of variation Cv in percentages of an average value on an axis 28. The limit 24 relates to yarns of the poorest quality and limit 26 to yarns of the best quality. From this it may be seen that, in the case of good quality yarns, as the yarn number increases the deviations from the average value increase less strongly than for poor quality yarns. Thus, it is possible to build up a picture of the quality of the yarn which it is desired to simulate. From this picture it is possible to infer for the relevant yarn from FIG. 7 the coefficient of variation for a specific yarn number from one of limits 24, 25, 26. If this is compared with the coefficient of variation for the output signal according to FIG. 8, a difference will probably be noted. From this a factor may be determined, by which the total output signal is multiplied, with which, therefore, any excursion of the signal at any one time is increased or reduced. Thus, a simulated signal arises, which is extensively adapted to real circumstances.

The adaptation of the yarn simulation to real circumstances may, however, be taken further. To this end, prior to combining, the frequency of each sine-wave generator (FIG. 8) may additionally be frequency-modulated with a random signal, such that a broader band signal arises. The band width of the random signal preferably corresponds to the channel spacing. In any case, yarns generally also comprise so-called rare occurrences such as neps, slubs, nips or impurities, which have not hitherto been taken into account. Such occurrences may be simulated with a random generator and added to the signal. The frequency and magnitude of such occurrences may be found for the respective occurrences in the publication "USTER STATISTICS", for example. Frequency values, as may be inferred from FIG. 9, for example, may be input into the random generator.

Figure 9:
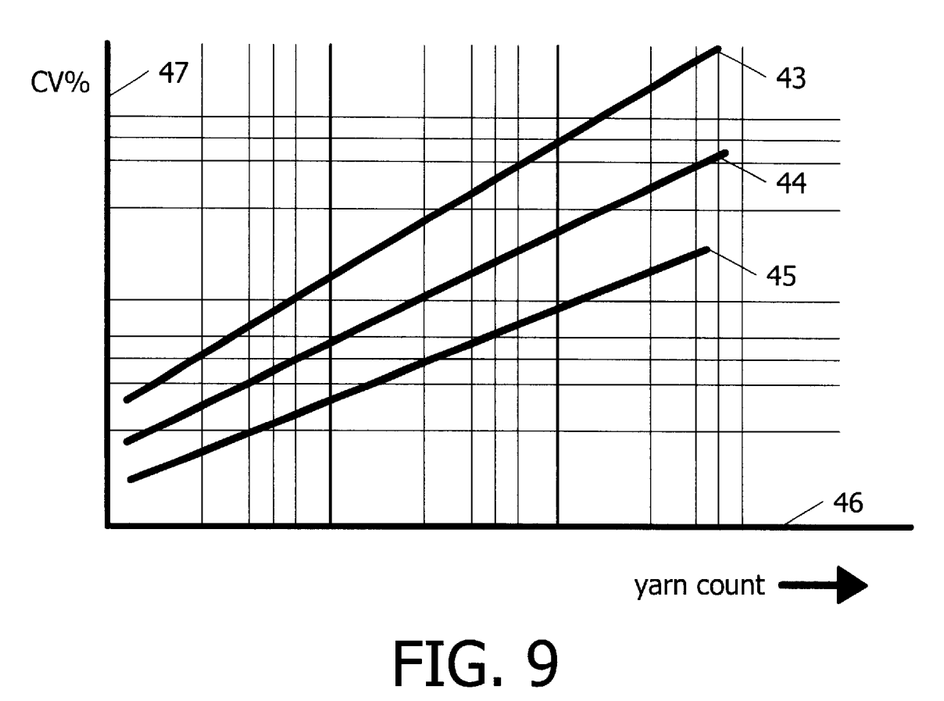
FIG. 9 is a graph associated with rare occurrences in the yarn.

FIG. 9 shows an example of a graph as may be found in the above-mentioned USTER STATISTICS, in addition to graphs according to FIGS. 6 and 7. This graph shows three limits 43, 44 and 45 for values which indicate a number of rare occurrences per yarn length. These values and limits are plotted with values for the yarn number over a horizontal axis 46 and with values for the number of occurrences per 1000 meters of yarn on an axis 47. The limit 43 relates to yarns of the poorest quality and limit 45 to yarns of the best quality. From this it may be seen that, in the case of good quality yarns, as the yarn number increases the number of occurrences increases less strongly than in the case of poor quality yarns. The addition of the random generator may be effected with a randomly generated amplitude and length, which quantifies the deviation of the occurrence from the average value. The random generator then outputs pulses which are superposed on the output signal according to FIG. 8 and which correspond to an empirical value for typical imperfections. FIG. 9 merely represents an example of a plurality of statistics which indicate, separately also, the frequency of special imperfections such as slubs, nips, neps, husk pieces, impurities, etc.

FIG. 10 shows, for example, a variation curve 48, known per se for yarn, for mass variations which are represented as deviating from an average value M. The method shown in FIGS. 2 to 8 provides such a variation curve 48 which is recorded along an axis 49, on which values for the yarn length are plotted. For each individual variation, which is represented by a vertical deviation, the height of which corresponds to the extent of the deviation from the average value M, the position in the yarn or along the yarn is also known. The variation curve 48 does not differ in type from a variation curve which was determined by measuring a yarn in a yarn tester. Thus, the individual variations or signal points or the values which they represent may be directly converted into pixels and strung together, such that simulation of a yarn arises. The deviations of the signal points provide a measure of the intensity of a color or a grey value. If several rows of such pixels are strung together, the image 51 (FIG. 1) arises, for example, from which individual rows 60, 61, 62 may be clearly seen, which are composed of pixels which here appear in two intensities or gradations, e.g. black or white. Image 52 arises in the same way, with the sole difference that the parameters or the measured signal which were converted into pixels originate from a yarn which serves as a reference and were determined by measuring the yarn in a yarn tester or by simulation. Accordingly, simulations of fabrics with different textures are also possible, for example knitted fabrics. The pixels of a yarn are then arranged in the image in accordance with the flow of the yarn in the respective fabric. Thus, just as in woven fabrics the warp and weft threads cross and therefore overlap, the threads or yarns in the knitted fabric form loops. In both cases, the overlap may or may not be taken into account in the simulation, by increased intensity at the relevant point.

Figure 11:
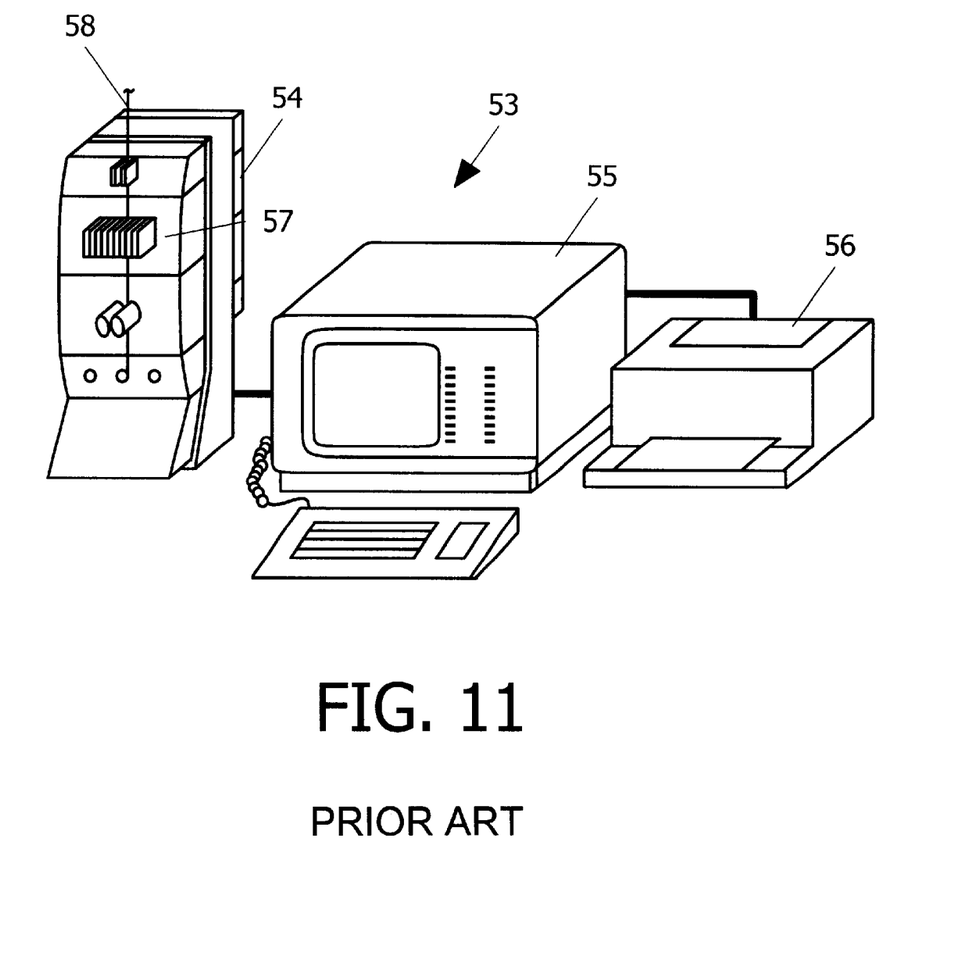
FIG. 11 shows a yarn testing apparatus.

FIG. 11 shows a yarn testing apparatus 53 known per se comprising the testing apparatus 54 proper, an evaluating and operating unit 55 and a printer 56. The testing apparatus 54 is provided with one or more measuring modules 57, which comprise measuring elements for the parameters to be investigated. A yarn 58, whose parameters, such as its mass, hairiness or structure for example, are to be continually measured, is conveyed in a known way through the measuring elements.

The method according to the invention may thus be summarized in a series of steps, as follows:

a) Generation of pixels for a reference yarn by measuring at least one relevant parameter on a reference yarn and subsequent conversion of the values of the parameter into values for the intensity of pixels which, when strung together, provide simulation of the reference yarn, or by generation of the pixels by calculation of the relevant parameters from statistical material such as average yarn values. Each pixel also has associated with it information about its position along the reference yarn.

b) Generation of pixels for a given yarn by measuring at least one relevant parameter on the given yarn and subsequent conversion of the values of the parameter into values for the intensity of pixels, which, when strung together, provide simulation of the given yarn. Each pixel also has associated with it information about its position along the given yarn.

c) Generation of a first image of a textile fabric by arranging the pixels of a yarn according to the yarn flow in the fabric, e.g. by laying next to each other the rows of pixels of a given yarn whose parameters have been measured.

d) Generation of a second image of a textile fabric by arranging the pixels of a yarn according to the yarn flow in the fabric, e.g. by laying next to each other the rows of pixels of the reference yarn.

e) Comparison of the first and second image by projecting them next to or over each other. It is also possible, at this point, to exchange the content of the first image for the content of the second image and vice versa, or continuously to cross-fade the images. Instead of starting from statistical values, as contained in the staple diagrams and spectrograms, it is also possible to start from simulation of a yarn signal. Each fibre could thus be replaced by a square pulse of the length of the fibre and a yarn signal generated by random distribution of these square pulses. In addition to the simulation of fabrics such as woven fabrics, knitted fabrics etc., it is also possible to simulate so-called yarn diagrams. Thus, it is possible to generate an image of a yarn diagram with a reference yarn and of a yarn diagram with a given yarn. Both the reference yarn and the given yarn may here also be simulated by measured parameters or calculated parameters.

It may be assumed that the overall calculation of the yarn signal for the reference yarn may be carried out in a computer, which may be programmed by a person skilled in the art for this purpose and for carrying out operations such as are illustrated with the aid of FIGS. 2 to 10.

The method according to the invention may be carried out in a device as shown in FIG. 11, if the evaluating and operating unit 55 has an appropriate program. If, for example, the parameters for one or more reference yarns are stored therein, an image of a woven or knitted reference fabric may be generated on the screen at any time. In addition, parameters of a real yarn 58 may be tested in the measuring module 57 and may likewise result, in the evaluating and operating unit 55, in an image of a simulated woven or knitted fabric. With the aid of known programs for image processing and representation, the two images may be output on the screen or by the printer 56 in such a way that a comparison is easily possible.

What is claimed is:

1. A method for assessing the effect of yarn defects on textile fabrics, by simulating an image of the fabric based on a given yarn, characterized in that a first fabric image (51) is generated by simulation based on multiple values of a first parameter of the given yarn, said values of the first parameter of the given yarn (58) being determined by measuring the yarn in a yarn testing apparatus (53), wherein for each value an indication is given of the place along the yarn to which a value relates;

in that a second fabric image (52) is generated by simulation based on values calculated from statistically determined yarn properties representing a reference yarn, wherein multiple values are calculated for said first parameter and for each value an indication is given of a place along the reference yarn to which a value relates; and in that the first fabric image is compared with the second fabric image.

2. A method according to claim 1, characterized in that a variation curve (48) for a parameter is determined by calculation.

3. A method according to claim 2, characterized in that a mass variation curve (48) is determined.

4. A method according to claim 2, characterized in that grey or color values are assigned to values from the variation curves.

5. A method according to claim 4, characterized in that grey or color values are converted into pixels and strung together in rows (60, 61, 62) to simulate a yarn and in that the rows are arranged according to the yarn flow in the fabric to simulate a fabric.

6. A method according to claim 1, characterized in that variation curves (48) for a simulated yarn are obtained from spectrogram curves (7, 8, 9, 10) and from staple diagrams (1).

7. A method according to claim 6, characterized in that rare occurrences are taken into account in the variation curves (48).

8. A method for assessing the effects of yarn defects on textile fabric, said method comprising:

determining a set of values of a first parameter of a given yarn and the location of each such value along the length of the given yarn by passing the given yarn lengthwise through a measuring station in a yarn testing apparatus, and converting said values into pixels strung together to simulate a first image representing a fabric made from the given yarn;

determining by calculation from statistically determined yarn properties a set of values of said first parameter for a reference yarn and the location of each such value along the length of the reference yarn, and converting said set of values of said first parameter of the reference yarn into pixels strung together to simulate a second image representing a fabric made from the reference yarn; and comparing said first fabric image with said second fabric image.

* * * * *